US00PP30242P2

(12) United States Plant Patent
Hansen

(10) Patent No.: US PP30,242 P2
(45) Date of Patent: Feb. 26, 2019

(54) ***ARUNCUS* PLANT NAMED 'FAIRY HAIR'**

(50) Latin Name: *Aruncus*
Varietal Denomination: Fairy Hair

(71) Applicant: Hans A. Hansen, Zeeland, MI (US)

(72) Inventor: Hans A. Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 10 days.

(21) Appl. No.: 15/731,996

(22) Filed: Sep. 5, 2017

(51) Int. Cl.
*A01H 5/02* (2018.01)

(52) U.S. Cl.
USPC ..... Plt./263.1
CPC ..... *A01H 5/02* (2013.01)

(58) Field of Classification Search
USPC ..... Plt./263.1
See application file for complete search history.

*Primary Examiner* — Anne Marie Grunberg

(57) ABSTRACT

The new hybrid *Aruncus* plant named 'Fairy Hair' with finely-dissected, dark green foliage holding well into the season. Light creamy buds transition to near white flowers on airy scapes above foliage. Plant habit is finely textured, short and very compact.

1 Drawing Sheet

Botanical denomination: *Aruncus*.
Cultivar designation: 'Fairy Hair'.

BACKGROUND OF THE INVENTION

The present invention relates to a new and distinct plant of goat's beard. The new plant was selected from initial evaluations by the inventor at a wholesale perennial nursery in Zeeland, Mich., USA in spring of 2011 from seedlings that were sown in the fall of 2009. The female parent is an unreleased proprietary hybrid between an unnamed selection (not patented) of *Aruncus aethusifolius* times *A. dioica* and the male parent is *Aruncus dioicus* 'Kneiffii' (not patented). The new plant passed the final evaluation in spring of 2014. The new plant was selected from among many other seedlings growing at the same nursery in Zeeland, Mich. which met the rigorous criteria of excellent foliage and habit established as breeding goals. 'Fairy Hair' has been asexually propagated since 2014 by shoot tip tissue culture at the same nursery in Zeeland, Mich. The resultant asexually propagated plants have remained stable and exhibit the identical characteristics as the original plant.

No plants of *Aruncus* 'Fairy Hair' have been disclosed or sold, under this or any name, in this country or anywhere in the world, prior to the filing of this application, with the exception of that which may have been disclosed within one year of the filing of this application and was either derived directly or indirectly from the inventor.

BRIEF SUMMARY OF THE INVENTION

'Fairy Hair' differs from all other goat's beard known to the applicant. Compared with the female parent the foliage is finer dissected and the habit is shorter and more compact than that all other goat's beard known to the inventor.

The nearest known cultivar to 'Fairy Hair' is *Aruncus* 'Misty Lace' U.S. Plant Pat. No. 15,798. Compared with the new plant, 'Misty Lace' is taller and broader in habit and the foliage is less finely dissected. Compared with co-pending application Ser. No. 15/732,106 *Aruncus* 'Chantilly Lace' the new plant is smaller in habit with finer leaf texture.

Compared with the female parent, the new plant is shorter and has finer textured foliage. Compared with the male parent, the new plant is slightly shorter.

The new plant, 'Fairy Hair', differs from all *Aruncus* known to the inventor in the following combined traits:

1. The foliage is finely-dissected, tri-pinnately compound, dark-green colored.
2. Flower are light creamy white on airy scapes above the plant.
3. Plant habit is short and very compact.

BRIEF DESCRIPTION OF THE DRAWINGS

The photographs of the new plant demonstrate the overall appearance of 'Fairy Hair' including the unique traits. The plant in the photograph is of a two-year-old plant grown in a shaded trial garden at a wholesale perennial nursery in Zeeland, Mich., USA. The colors are as accurate as reasonably possible with color reproductions. Some slight variation of color may occur as a result of lighting quality, intensity, wavelength, and direction or reflection.

DETAILED BOTANICAL DESCRIPTION

Figure 1:
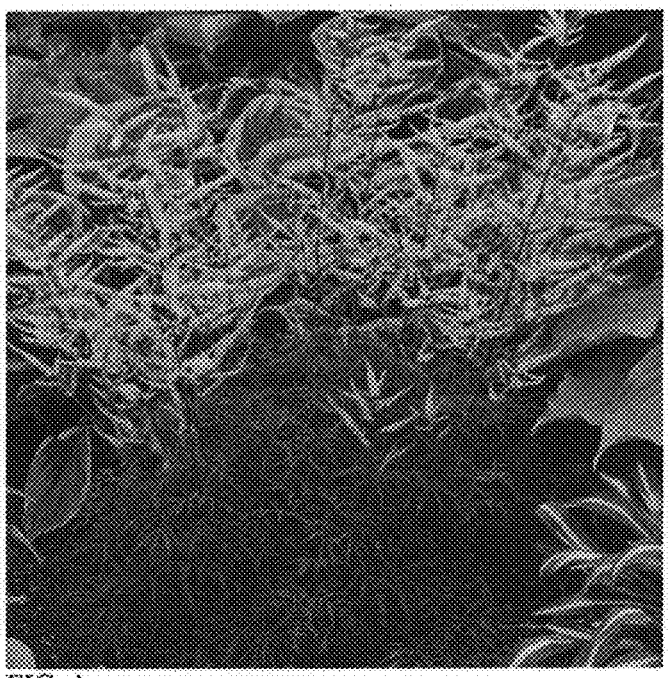
FIG. 1 shows the habit in spring flower together with the fine textured bipinnately compound leaves.
Figure 2:
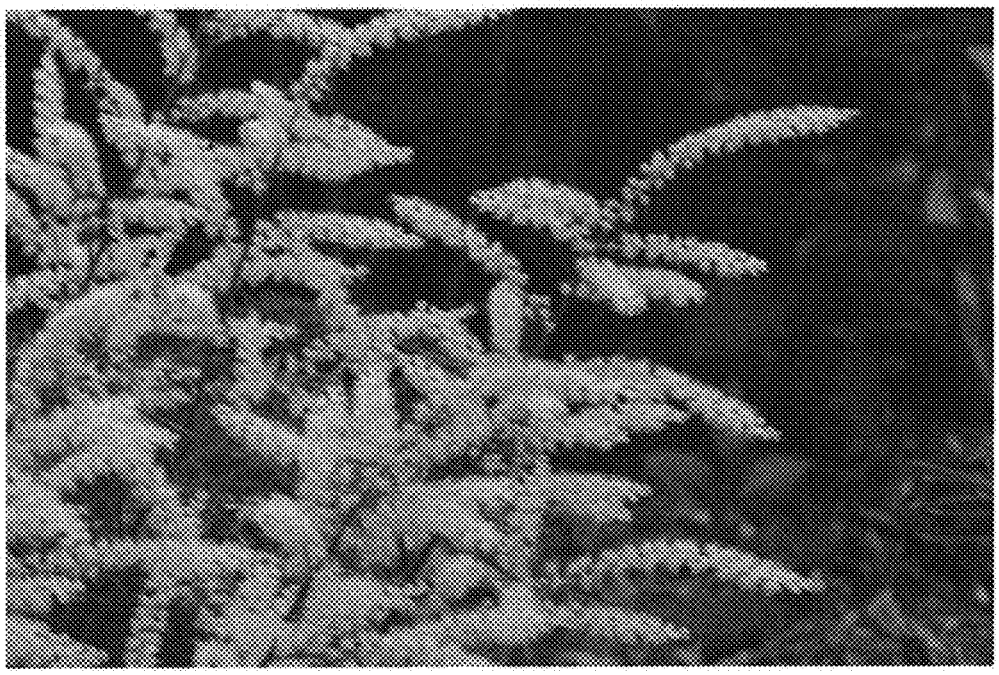
FIG. 2 shows a close-up of the flowers and buds.

The following description is based on two-year-old plants growing in a double poly greenhouse with supplemental water and fertilizer at a wholesale perennial nursery in Zeeland, Mich., USA. The new plant has not been grown under all possible environments and may phenotypically appear different under different conditions such as light, temperatures, fertilizer, and water, without any difference in genotype. The color descriptions are from the 2015 edition of The Royal Horticultural Society Colour Chart except where common dictionary terms are used.

Parentage: The female (seed parent) is an unreleased proprietary hybrid between an unnamed selection (not patented) of *Aruncus aethusifolius* times *A. dioica*; the male (pollen parent) is *Aruncus dioicus* 'Kneiffii' (not patented);

Plant habit: Hardy herbaceous perennial of dense short stems producing compact mounded habit; foliage about 20.0 cm tall and 40.0 cm diameter;

Roots: Fibrous, finely branched; light tan in color depending on soil type;

Growth rate: Moderate, from tissue culture liner to finishing in three-liter container in about 3 months; beginning to flower in 6 to 8 weeks following a 9 week vernalization;

Stems: About 60 to 90 per plant; non-flowering stems to about 3.3 cm long and 3.5 mm diameter; flowering stems to about 8.5 cm long before peduncle and 3.5 mm diameter;

Stem color: Between RHS 145D and RHS 144D;

Internode: Variable from 1.5 cm on branched flowering stems to 2.0 mm on young stems;

Internode color: Between RHS 145D and RHS 144D;

Foliage: Blade or lamina glabrous abaxial and adaxial; tri-pinnately dissected; typically with five pinna;

Pinna: Basal pinna to 5.0 cm long and 4.0 cm wide with distal lobes to 4.0 cm long and 2.5 mm wide, decreasing in pinna length and width and pinnule length distally; typically pinnule five-lobed and individual lobes dissected to dentate with teeth about 2.0 mm long; pinnule apex narrowly acute; pinnule base on pinna radius;

Petiole: Terete; glabrous; swollen at base; to about 12.8 cm long, 1.0 mm across in middle and 4.0 mm across at base; average about 9.0 cm long, 1.0 mm across in middle and 3.5 mm across at base;

Rachis: Glabrous; terete to slightly applanate adaxial; upright; to about 12.5 cm long and 1.5 mm wide before base, swollen at base to about 3.5 mm wide; average about 8.0 cm long and 1.5 mm wide before base and swollen base to about 3.0 mm wide;

Rachis and petiole color: Nearest RHS 146D abaxial and nearest RHS 146A adaxial;

Pinna rachis: Glabrous; slightly concavo-convex; about 10.0 mm long and about 0.5 mm wide on proximal pinnule and about 2.0 mm long and 0.5 mm wide on distal pinnule;

Pinna rachis color: Nearest RHS 146C abaxial and RHS 146A adaxial;

Foliage color: Leaf color is seasonally variable; young expanding leaves adaxial and abaxial surfaces nearest RHS 144A; mid-season to fall adaxial nearest RHS 139A and abaxial nearest RHS 137A;

Pinnule: Narrowly lobed; terminal to about 4.0 cm long and 2.5 mm across; nearly lanceolate except for thin side lobes;

Pinnule margin: Dissected;

Pinnule apex: Narrowly acute;

Pinnule base: Truncate with pinna rachis;

Leaf surface: Glabrous adaxial and abaxial; dull, matte;

Leaf quantity: Dense, diameter with up to 14 leaves per stem;

Veins: Pinnate; glabrous adaxial and abaxial;

Vein color: Adaxial nearest RHS 151D and abaxial nearest RHS 146D;

Inflorescence: In alternately, loosely-branched, airy panicle; about 10 panicles per plant with about 600 flowers per panicle; first panicle flowering beginning in late spring; individual panicles remaining in flower for about three to four weeks; flower attitude mostly outwards; individual flowers remaining effective for about 4 days;

Fragrance: None detected;

Peduncle: Terete, erect; glabrous; to about 33.0 cm tall and 3.5 mm diameter at base; flowering portion about 16.0 cm long and 10.0 cm across;

Peduncle attitude: Main panicle upright, panicle branches slightly drooping;

Peduncle branches: Terete; glabrous; to about 6.5 cm long and 1.0 mm diameter;

Peduncle color: Nearest RHS137A;

Pedicel: Terete; glabrous; to about 1.0 mm long and 0.5 mm in diameter;

Pedicel color: Nearest RHS 146C;

Buds one day prior to opening: Ellipsoid to globose with rounded apex, and rounded base; about 2.5 mm diameter;

Bud color: Nearest RHS NN155A;

Flower: Campanulate, actinomorphic; individual flowers lasting about three to four days on plant or as cut panicle;

Calyx: Campanulate; five sepals;

Sepals: Five; lanceolate; acute apex; truncate base; glabrous abaxial and adaxial; about 1.0 mm long and 0.5 mm wide at base;

Sepal color: Abaxial and adaxial blend between RHS 155A and RHS 10D;

Petals: Five; obelliptic; acute apex, narrow attenuate base; margin entire; finely puberulent outside and glabrous inside; about 1.5 mm long and 0.5 mm wide;

Fruit and seed: Not observed;

Disease and pest tolerance: *Aruncus* 'Fairy Hair' grows best with ample moisture and good drainage in part shade or protection from sun in the hottest part of the day. Cold hardy from USDA zones 3 to 7. Other pest and disease resistance and tolerance outside of that normal for *Aruncus* is not known at this time.

It is claimed:

1. The new and distinct ornamental plant named *Aruncus* 'Fairy Hair' as herein described and illustrated.

* * * * *